United States Patent [19]

Lányi et al.

[11] Patent Number: 5,235,109
[45] Date of Patent: Aug. 10, 1993

[54] PROCESS FOR THE PREPARATION OF KETONE COMPOUNDS

[75] Inventors: György Lányi; Tamás Kállay; László Ledniczky; Lajos Imrei; Éva Somfai; Tibor Montay; Róbert Gépész; Valéria Dénes née Lustig; László Árvai, all of Budapest, Hungary

[73] Assignee: Chinoin Gyogyszer- Es Vegyeszeti Termekek Gyara RT, Budapest, Hungary

[21] Appl. No.: 793,422

[22] PCT Filed: Apr. 18, 1990

[86] PCT No.: PCT/HU90/00026
§ 371 Date: Dec. 11, 1991
§ 102(e) Date: Dec. 11, 1991

[87] PCT Pub. No.: WO91/16293
PCT Pub. Date: Oct. 31, 1991

[51] Int. Cl.$^5$ ............................................. C07C 45/45
[52] U.S. Cl. .................................................... 568/322
[58] Field of Search ........................................ 568/322

[56] References Cited

U.S. PATENT DOCUMENTS

| 4,053,517 | 10/1977 | Reininger et al. | 568/322 |
| 4,268,691 | 5/1981 | Fung et al. | 568/322 |
| 4,508,924 | 4/1985 | Mueller et al. | 568/322 |
| 5,068,447 | 11/1991 | Gors et al. | 568/322 |

OTHER PUBLICATIONS

Scheilhauser, Pharmazie, vol. 43 (2), pp. 86–90 (1988).
Dauksas et al, Chem. Abst., vol. 109, #17006y (1988).

Primary Examiner—James H. Reamer
Attorney, Agent, or Firm—Herbert Dubno; Jonathan Myers

[57] ABSTRACT

The invention relates to an improved, large scale process for the preparation of compounds of formula (I)

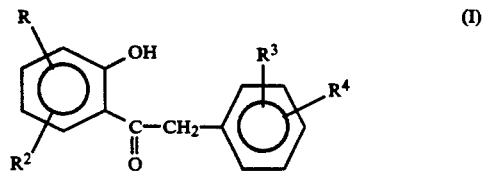

wherein
R is halogen atom or hydroxyl,
$R^2$ is hydrogen atom or hydroxyl,
$R^3$ and $R^4$ are hydrogen or alkoxy having 1–6 carbon atoms.

4 Claims, No Drawings

PROCESS FOR THE PREPARATION OF KETONE COMPOUNDS

CROSS REFERENCE TO RELATED APPLICATION

This application is a national phase of PCT/HU90/00026 filed Apr. 18, 1990.

FIELD OF THE INVENTION

The invention relates to an improved, large scale process for the preparation of ketones of formula (I)

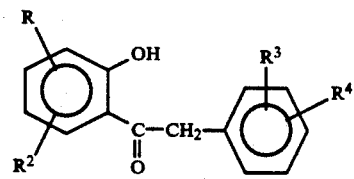

wherein
R is halogen atom or hydroxyl,
$R^2$ is hydrogen atom or hydroxyl,
$R^3$ and $R^4$ are hydrogen atom or alkoxy having 1–6 carbon atoms.

BACKGROUND OF THE INVENTION

It is known that the ketones of formula (I) can be used as intermediates for the preparation of isoflavone derivatives (see e.g. HU PS No. 163,515) as well as anabolics since they effect metabolism.

From an industrial point of view those processes are the most advantageous wherein resorcinol is used as starting material, e.g. the desired product may be obtained according to the Houben-Hoesch reaction: wherein the resorcinol is reacted in anhydrous medium with benzyl cyanide in the presence of dry hydrogen chloride gas and anhydrous tin chloride (see e.g. J. Chem. Soc. /1923/, 404 and J. Am. Chem. Soc. 48, 1926, 791). The yield in this reaction is 50% and the drawback of this process is that the hydrolysis of the "ketimine" derivate intermediate is a very corrosive procedure.

Alternatively 2-hydroxy-4-n-butoxy-phenyl-benzyl ketone or 4-hydroxy-2-n-butoxy-phenyl-benzyl ketone may be obtained when reacting the mono-n-butyl ether of resorcinol with phenyl-acetyl-chloride in the presence of pyridine, then removing pyridine by distillation, dissolving the residue in ether, extracting the solution with hydrogen chloride several times, removing the ether by distillation, thereafter treating the 1-phenyl-acetyloxy-4-n-butyloxy-phenol thus obtained in nitrobenzene with aluminum chloride and steam distilling the mixture thus obtained (see Example 7 of HU PS No. 168,744). The starting material of the first step, i.e. the mono-n-butyl ether of resorcinol, can be obtained e.g. when reacting resorcinol with n-butyl bromide in the presence of dimethyl formamide. Regarding that from resorcinol diether derivatives may also be formed, in order to obtain an end product of good quality, the monoethers have to be purified before the second reaction step.

The analogous phenol compound can be prepared by the known, so called Bouveault reaction too, wherein 2 moles of anhyrous aluminium chloride are reacted with phenol. In the first step of this reaction phenoxy-aluminium dichloride forms while hydrogen chloride gas is released. In the second reaction step said phenoxy-aluminium dichloride is then reacted with the acid chloride derivative in the presence of a further mole of aluminium chloride (Oláh, Gy:Friedel Crafts and related reactions, Vol. I, page 97, 1963).

The drawbacks of these known processes are as follows:
- the reaction procedure itself and the technology too, are rather difficult,
- large amounts of aluminum chloride (2 moles) is required,
- the released hydrogen chloride is corrosive.

DESCRIPTION OF THE INVENTION

The present invention relates to a process for the preparation of ketones of formula (I) and salts thereof

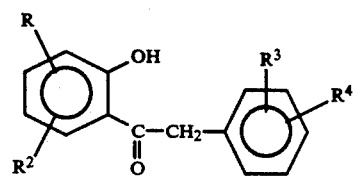

wherein R, $R^2$, $R^3$, $R^4$, $R^6$ are the same as mentioned above wherein phenols of formula (II)

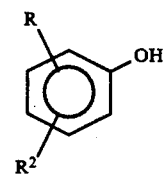

are reacted with acid chlorides of the formula (IV)

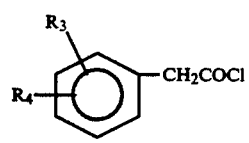

in the presence of inert, anhydrous organic solvent and anhydrous aluminum chloride by a method known per se, the mixture thus obtained is decomposed with an aqueous acid solution and the phases obtained are separated. According to the invention the phenol derivative is reacted with 1 mole aluminum chloride—calculated for the phenol derivative—at a temperature between 0° C. and 40° C. in the presence of halogenated hydrocarbon, preferably dichloroethane. Thereafter the complex of the formula (III) thus obtained

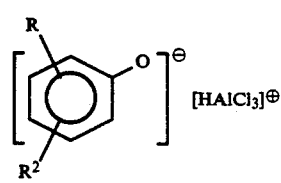

is reacted with an acid chloride of the formula (IV)

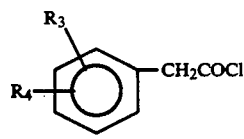

(IV)

preferably in the presence of the solvent used previously at a temperature ranging from 10° C. to 60° C., thereafter adding an aqueous acid solution to the mixture thus obtained, separating the phases and recovering the desired ketone compound from the organic layer.

We have surprisingly discovered that when reacting e.g. resorcinol with 1 mole of anhydrous aluminum chloride, without hydrogen chloride formation a hydrogen-aluminum-trichloro-3-hydroxy phenolate (referred to hereinafter simply as "complex") is obtained, which dissolves in the reaction medium used. This complex is very active and it is able to react with the acid chloride without adding additional aluminum chloride.

The process of the invention is based on the above recognition and phenol derivatives of formula (II) are used as starting material.

In the process according to the invention halogenated hydrocarbons, preferably dichloroethane, are used as solvent in 3 to 10-fold excess. The reaction temperature depends on the used starting material; in the case of resorcinol and dichloroethane the reaction is preferably carried out at a temperature of 10° to 25° C.

The reaction of the complex with the acid chloride can be carried out by adding the aromatic acid chloride or the solution thereof to the solution or to the suspension of the complex or alternatively the solution or suspension of the complex can be added to the acid chloride or to the solution of same.

In a preferred embodiment of the process according to the invention the preparation of the complex and the subsequent reaction steps are carried out in the same aprotic solvent, preferably in halogenated hydrocarbons.

Another important recognition of the present invention enables the pure isolation of the desired product. We have found that the ketones of the formula (I), which are obtained from the resorcinol derivatives of the formula (V)

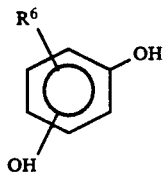

(V)

wherein $R^6$ is hydrogen atom or hydroxyl
can react with potassium carbonate to form the double salts of formula (VI)

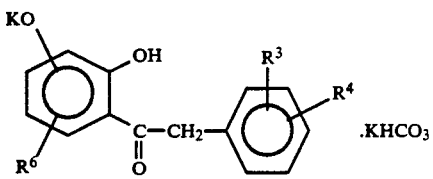

(VI)

wherein $R^3$, $R^4$ and $R^6$ are the same as mentioned above
which are not soluble in aprotic solvents. So, according to a preferred embodiment of the process according to the present invention, the product is isolated (e.g. separated by filtration) in the form of this salt and so can selectively be separated from the side products or other accompanying materials which are present or are formed in the reaction mixture. The ketone of formula (I) can be obtained from the double salt of formula (VI) after dissolving it in water and acidifying the solution thus obtained to pH=3.5–4.5.

The above mentioned step is especially preferred if the starting resorcinol or acid chloride are not sufficiently pure. When pure starting material is used, ketones of appropriate quality can be obtained by the optional removal of the solvent of the organic layer and by recrystallization, preferably from toluene, of the residue.

The advantages of the present invention are e.g. as follows:
the synthesis can be carried out without the separation of the intermediates, especially without the preparation of the mono-n-butyl ether of resorcinol and without the use of nitromethane, nitrobenzene or ether solvents,
the amount of the aluminium chloride is decreased to the half of the amount used in the known processes,
the considerable corrosion of the Houben-Hoesch method can be eliminated,
the yield amounts to 82–85%, which is substantially higher than that of any known method,
the quality of the product is very good.

SPECIFIC EXAMPLES

The process according to the invention is illustrated in detail by the following Examples.

EXAMPLE 1

55 g (0.5 mole) of resorcinol were suspended in 250 ml of dichloro ethane and at 20° C. 67 g (0.502 mole) of anhydrous aluminum chloride were added. To the obtained homogeneous dark solution, containing the hydrogen-aluminum-trichloro-3-hydroxy-phenolate, 77.2 g (0.5 mole) of phenyl-acetyl chloride in 100 ml of dichloro ethane were added over one hour while the temperature raised to 35°–40° C. The reaction mixture was stirred for one hour, the solution thus obtained was added to an aqueous hydrochloric acid solution, the two layers were separated, the organic layer was washed with water to neutral, the solvent was distilled off and the residue was optionally crystallized from toluene. 96.9 g of 2,4-dihydroxy-phenyl-benzyl-ketone were obtained, m.p.: 112°–114° C., yield: 85%. After an optional recrystallization from toluene the melting point was 113°–114° C. Elemental analysis for $C_{14}H_{12}O_3$ (Mw: 228):

Calculated: C %: 73.68, H %: 5.26. Found: C %: 73.6, H %: 5.3.

NMR spectrum (Bruker WP 80 spectrometer, in DMSO-$D_6$ solvent, TMS internal standard):

$^1H$
6 C—H 7.90 ppm /d/ $^3J$-9Hz
5 C—H 6.37 ppm /dd/
3 C—H 6.25 ppm /d/ $^4J$-2Hz
$^{13}C$ -continued 4-C 165.1 ppm

Example 2

The procedure described in Example 1 was followed. After separating the two phase mixture, the organic layer was washed to neutral with water, the dichloroethane layer was separated and 69 g (0.5 mole) of anhydrous potassium carbonate were added. From the reaction mixture the precipitated 2,4-dihydroxy-phenyl-benzyl-ketone-potassium-potassium hydrogencarbonate double salt ($C_{14}H_{11}O_3K \cdot KHCO_3$) was separated by filtration (166 g), was dissolved in methanol:water=1:3 and the solution thus obtained was acidified (pH=4) with 33% acetic acid. The precipitated product was filtered and after drying 96.2 g of 2,4-dihydroxy-phenyl-benzyl-ketone were obtained, m.p. 113°-114° C. The quality of the product thus obtained was identical with the product of Example 1 obtained after recrystallization. The melting point of a mixture (1:1) did not show depression.

Elemental analysis for $C_{14}H_{11}O_3K \cdot KHCO_3$ (Mw:366): Calculated: C %: 49.18, H %: 3.27. Found: C %: 49.6 H %: 3.32.

| NMR spectrum: |
| --- |
| $^1H$ |
| 6 C—H 7.63 ppm /d/ $^3J=9Hz$ |
| 5 C—H 6.00 ppm /dd/ |
| 3 C—H 5.78 ppm /d/ $^4J=2Hz$ |
| $^{13}C$ |
| 4-C 174.2 ppm |

The potassium salt in the double salt of 2,4-dihydroxy-phenyl-benzyl ketone appears in the 4-position.

EXAMPLE 3

64.25 g (0.5 mole) of 2-chlorophenol were dissolved in 200 ml of dichloroethane and 67 g (0.5 mole) of anhydrous aluminum chloride were added to the solution. Thereafter 77.2 g (0.5 mole) of phenyl-acetyl chloride in 100 ml of dichloroethane were added over 1 hour under stirring while the reaction temperature raised from 15°-20° C. to 35°-40° C. After a one-hour stirring the reaction mixture was admixed with aqueous hydrogen chloride, the two-phase mixture was separated, the organic layer was washed with water to neutral and the solvent was removed. 106.1 g of 2-hydroxy-3-chlorophenyl-benzyl-ketone were obtained, m.p.: 62°-64° C. After a recrystallization from aqueous isopropanol (1:2), m.p. 63°-67° C.

Elemental analysis for $C_{14}H_{11}ClO_2$ (Mw:246.5): Calculated: C %: 68.15, H %: 4.46, Cl %: 14.40. Found: C %: 68.55, H %: 4.70, Cl %: 14.00.

Example 4

22 g (0.2 mole) of hydroquinone were dissolved in 60 ml of dichloroethane and 26.8 g (0.2 mole) of anhydrous aluminum chloride were added to the solution. To the obtained complex 30.8 g (0.2 mole) of phenyl-acetyl chloride in 30 ml of dichloroethane were added. Further the procedure of Example 1 was followed. 10.1 g of 2,5-dihydroxy-phenyl-benzyl-ketone were obtained, m.p.: 118°-120° C.

Elemental analysis for $C_{14}H_{12}O_3$ (Mw: 228): Calculated: C %: 73.68, H %: 5.26. Found: C %: 73.62, H %: 5.58.

EXAMPLE 5

24.7 g (0.196 mole) of floroglucinol were dissolved in 70 ml of dichloroethane and 26.6 g (0.2 mole) of anhydrous aluminum chloride were added to the solution. To the obtained complex 30.1 g (0.196 mole) phenyl-acetyl-chloride in 30 ml of dichloroethane were added. Further the procedure of Example 1 was followed.

15 g of 2,4,6-trihydroxy-phenyl-benzyl-ketone were obtained, m.p.: 117°-120° C.

Elemental analysis for $C_{14}H_{12}O_4$ (Mw: 244): Calculated: C %: 68.85, H %:4.92. Found: C %: 69.05, H %: 4.67.

EXAMPLE 6

120 kg (1.09 kmole) of resorcinol were suspended in 660 l of dichlorethane and 150 kg (1.12 kmole) of anhydrous aluminum chloride were added to the suspension while the temperature raised from 15° C. to 25° C. The complex obtained dissolved in the reaction medium. 171 kg (1.10 kmole) of phenyl-acetyl chloride were added over a period of one hour while the temperature raised to 35°-40° C. The mixture was stirred for one hour thereafter it was admixed with diluted hydrogen chloride (the mixture of 300 l of hydrogen chloride and 600 l of water), and it was treated as described in the preceding Examples. The solvent was removed by distillation, the residue was recrytallized from toluene, the product obtained was centrifuged and dried at 45°-50° C. 205-210 kg of 2,4-dihydroxy-phenyl-benzyl-ketone were obtained, yield 82-84.5%. Calculated amount: 248.5 kg. The physical data are identical with the data given in Example 1.

EXAMPLE 7

27.5 g (0.25 mole) of resorcinol were suspended in 150 ml of dichloroethane and 33.5 g (0.25 mole) of anhydrous aluminum chloride were added. To the solution containing the formed complex 42.9 g (0.2 mole) crude 3,4-dimethyl-phenyl-acetyl-chloride in 50 ml of dichloroethane were added and was stirred for 4 hours. Thereafter the complex was decomposed by adding 1:1 aqueous hydrogen chloride, the dichloro ethane solution containing the desired product was washed with water, the solvent was removed and the residue was recrystallized from toluene. 45.9 g product were obtained, m.p.: 171°-173° C., yield 79.8%. Calculated amount: 57.6 g.

Elemental analysis for $C_{16}H_{16}O_5$ (Mw: 288): Calculated: C %: 66.66, H %: 4.17. Found: C %: 66.45, H %: 4.10. The NMR spectrum proved the desired compound.

TLC: Developing system: toluene/n-butyl acetate/acetic acid=8/2/1.

Adsorbent: Kieselgel 60 $F_{254}$ (Merck).

Application: 0.2 g/10 ml dimethyl formamide-100 μg.

Front: 16 cm.

Development in UV-light, 254 nm.

$R_f \sim 0.6$.

EXAMPLE 8

27.5 g (0.25 mole) resorcinol were suspended in 150 ml of dichloroethane and 33.5 g (0.25 mole) of anhydrous aluminum chloride were added to it. To the solution containing the obtained "complex" 48.5 g (0.2 mole) of 3,4-diethoxy-phenyl-benzyl-acetyl chloride in 50 ml of dichloroethane were added. Thereafter the procedure described in Example 7 was followed. 53.7 g of 2,4-dihydroxy-3',4'-diethoxy-phenyl-benzyl-ketone were obtained after a recrystallization from toluene, m.p.: 141°-143° C. Theoretical amount: 63.2 g. Yield 85%.

Elemental analysis for $C_{18}H_{20}O_5$: Calculated: C %: 68.55, H %: 6.23. Found: C %: 68.35, H %: 6.29.

The NMR data corresponds to the desired product.

TLC: (carried out as described in Example 7): $R_f \sim 0.7$.

What we claim is:

1. A process for the preparation of a compound of the Formula (I)

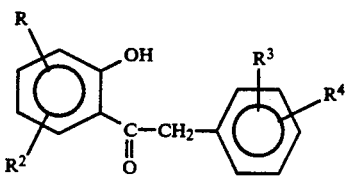

wherein
R is halogen or hydroxyl;
$R^2$ is hydrogen or hydroxyl; and
$R^3$ and $R^4$ are each hydrogen or $C_1$ to $C_6$ alkoxy;
which comprises the steps of:
(a) reacting a compound of the Formula (II)

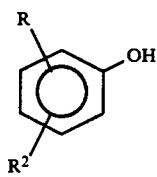

with an equimolar amount of anhydrous aluminum chloride in dichloroethane at a temperature between 0° C. and 45° C. to obtain in solution a complex of the Formula (III)

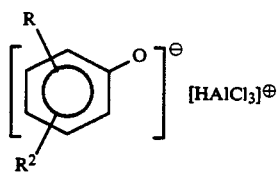

(b) acylating the complex of the Formula (III) with a compound of the Formula (IV)

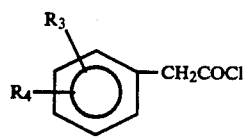

in dichloroethane at a temperature of 10° to 60° C. to obtain a compound of the Formula I; and
(c) thereafter adding an aqueous acid solution to the product of step (b) to separate the product into two phases, an aqueous phase and an organic phase, and recovering the compound of the Formula (I) from the organic phase by evaporation and recrystallization.

2. The process defined in claim 1 wherein according to step (b) the complex of the Formula (III) is acylated with phenyl acetyl chloride at a temperature of 20° to 50° C.

3. A process for the preparation of a compound of the Formula (Ia)

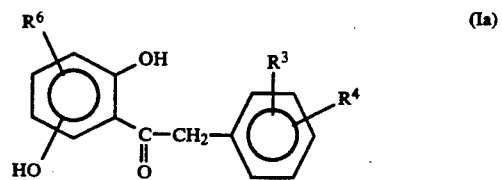

wherein
$R^6$ is hydrogen or hydroxyl; and
$R^3$ and $R^4$ are each hydrogen or $C_1$ to $C_6$ alkoxy;
which comprises the steps of:
(a) reacting a compound of the Formula (V):

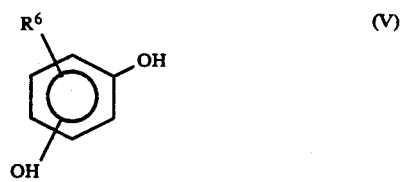

wherein $R^6$ hydrogen or hydroxyl, with an equimolar amount of anhydrous aluminum chloride in dichloroethane at a temperature between 0° C. and 45° C. to obtain in solution a complex of the Formula (IIIa)

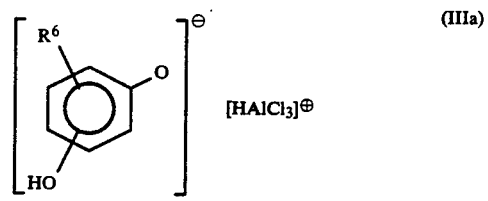

(b) acylating the complex of the Formula (III) with a compound of the Formula (IV)

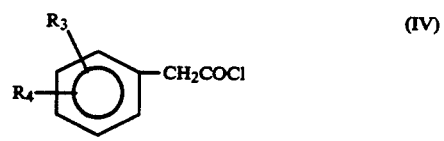

in dichloroethane at a temperature of 10° to 60° C. to obtain a compound of the Formula I;
(c) thereafter adding an aqueous acid solution to the product of step (b) to separate the product into two phases, an aqueous phase and an organic phase containing the compound of the Formula (I);
(d) reacting said organic phase with potassium carbonate, to form an insoluble double salt of the Formula (VI)

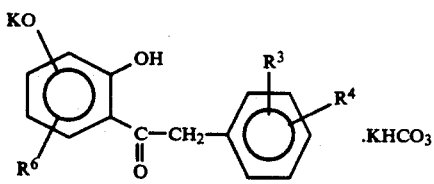
(VI)
and
(e) separating said insoluble double salt from said organic phase, dissolving the double salt in an aqueous alcohol solution, acidifying the solution to a pH of 3.5 to 4.5, and precipitating the desired compound of the Formula (I).
4. The process defined in claim 3, wherein according to step (e), the insoluble double salt is separated from said organic phase by filtration.
* * * * *